(12) United States Patent
Simard et al.

(10) Patent No.: US 8,187,817 B2
(45) Date of Patent: May 29, 2012

(54) DIAGNOSIS, TREATMENT, AND PREVENTION OF VASCULAR DISORDERS USING IL-1 AUTOANTIBODIES

(75) Inventors: John Simard, Austin, TX (US); Klaus Bendtzen, Lynge (DK)

(73) Assignee: XBiotech, Inc., Vancouver, BC (CA)

( * ) Notice: Subject to any disclaimer, the term of this patent is extended or adjusted under 35 U.S.C. 154(b) by 0 days.

(21) Appl. No.: 11/997,496

(22) PCT Filed: Jul. 26, 2006

(86) PCT No.: PCT/IB2006/002038
§ 371 (c)(1),
(2), (4) Date: Oct. 20, 2008

(87) PCT Pub. No.: WO2007/015128
PCT Pub. Date: Feb. 8, 2007

(65) Prior Publication Data
US 2009/0123415 A1  May 14, 2009

Related U.S. Application Data

(60) Provisional application No. 60/704,450, filed on Aug. 2, 2005.

(51) Int. Cl.
*A61K 38/20* (2006.01)
*A61K 39/395* (2006.01)
*A61P 9/10* (2006.01)

(52) U.S. Cl. .... 435/7.1; 435/7.92; 435/7.93; 424/133.1; 424/158.1

(58) Field of Classification Search ........................ None
See application file for complete search history.

(56) References Cited

U.S. PATENT DOCUMENTS

| | | | |
|---|---|---|---|
| 4,634,664 A | 1/1987 | Oestberg | |
| 4,965,198 A | 10/1990 | Yamasaki | |
| 5,034,316 A | 7/1991 | Weisbart | |
| 5,168,062 A | 12/1992 | Stinski | |
| 5,231,024 A | 7/1993 | Moeller | |
| 5,585,089 A | 12/1996 | Queen | |
| 5,654,407 A | 8/1997 | Boyle | |
| 5,693,762 A | 12/1997 | Queen | |
| 5,795,967 A | 8/1998 | Aggarwal | |
| 5,932,188 A | 8/1999 | Snow | |
| 5,959,085 A | 9/1999 | Garrone | |
| 6,090,382 A | 7/2000 | Salfeld | |
| 6,140,470 A | 10/2000 | Garen et al. | |
| 6,623,736 B2 | 9/2003 | Tobinick | |
| 2003/0026806 A1 | 2/2003 | Witte | |
| 2003/0040617 A9 | 2/2003 | Rosen | |
| 2003/0232054 A1 | 12/2003 | Tang | |
| 2004/0097712 A1 | 5/2004 | Varnum | |
| 2004/0185514 A1 | 9/2004 | Frostegard | |
| 2005/0054019 A1 | 3/2005 | Michaud | |
| 2005/0147603 A1 | 7/2005 | Smith | |
| 2006/0159775 A1 | 7/2006 | McGrath | |
| 2007/0071675 A1 | 3/2007 | Wu | |
| 2008/0050310 A1 | 2/2008 | Ebens, Jr. | |
| 2009/0191149 A1 | 7/2009 | Simard | |
| 2009/0298096 A1 | 12/2009 | Simard | |
| 2010/0040574 A1 | 2/2010 | Simard | |
| 2010/0068212 A1 | 3/2010 | Simard | |
| 2011/0008282 A1 | 1/2011 | Simard | |

FOREIGN PATENT DOCUMENTS

| | | |
|---|---|---|
| EP | 0659766 | 6/1995 |
| WO | 9006371 | 6/1990 |
| WO | WO 96/35719 | 11/1996 |
| WO | WO 2004/100987 | 11/2004 |
| WO | WO 2007/039552 | 4/2007 |
| WO | 2007132338 | 11/2007 |
| WO | 2007135546 | 11/2007 |
| WO | 2009148575 | 12/2009 |
| WO | 2010030979 | 3/2010 |

OTHER PUBLICATIONS

Clinton et al, American Journal of Pathology, Apr. 1991, vol. 138, No. 4, pp. 1005-1014.*
Von Der Thusen et al, Pharmacological Reviews, 2003, vol. 55, No. 1, pp. 133-166.*
Kasahara et al, The Journal of Immunology, 1987, vol. 138, No. 6, pp. 1804-1812.*
Wake et al, Recent Patents on Cardiovascular Drug Discovery, 2009, vol. 4, pp. 234-240.*
P Miossec, Annals of the Rheumatic Diseases, 2002, vol. 61, pp. 577-579.*
Bendtzen et al., "High-avidity autoantibodies to cytokines," *Trends Immunol. Today 19*, 209-11, May 1998.
Bendtzen et al., "Detection of autoantibodies to cytokines," *Mol. Biotechnol. 14*, 251-61, 2000.
Dardik et al., "Shear stress-stimulated endothelial cells induce smooth muscle cell chemotaxis via platelet-derived growth factor—BB and interleukin-lalpha," *J. Vascular surg. 41*, 321-31, Feb. 2005.
Dinarello, "Modalities for Reducing Interleukin 1 Activity in Disease," *Trends Pharmacol. Sci. 14*, 155-59, May 1, 1993.
Dinarello et al., "Anticytokine Strategies in the Treatment of the systemic Inflammatory Response Syndrome," *J. Am. Med. Assoc. 269*, 1829-35, Apr. 14, 1993.
Dinarello, "Biologic Basis for Interleukin-1 in Disease," *Blood 87*, 2095-147, 1996.
Dinarello, "Therapeutic strategies to reduce IL-1 activity in treating local and systemic inflammation," *Curr. Opinion Pharmacol. 4*, 378-85, 2004.
Larrick & Bourla, "Prospects for the Therapeutic Use of Human Monoclonal Antibodies," *J. Biol. Response Modifiers 5*, 379-93, 1986.
Garrone et al., "Generation and characterization of a human monoclonal autoantibody that acts as a high affinity interleukin-1α specific inhibitor," *Mol. Immunol. 33*, 649-58, 1996.
Griffiths et al., "Human anti-self antibodies with high specificity from phage display libraries," *EMBO J. 12*, 725-34, 1993.

(Continued)

*Primary Examiner* — Bridget E Bunner
*Assistant Examiner* — Fozia Hamud
(74) *Attorney, Agent, or Firm* — Stanley A. Kim

(57) ABSTRACT

Methods of detecting individuals at risk for atherosclerosis and related vascular diseases involving the detection of IL-1α autoantibodies, as well as therapeutic methods to prevent or treat atherosclerosis and related vascular disease by administering a pharmaceutical composition comprising IL-1α autoantibodies.

14 Claims, No Drawings

OTHER PUBLICATIONS

Hansen et al., "Sex- and age-dependency of IgG auto-antibodies against IL-1α in healthy humans," Eur. J. Clin. Invest. 24, 212-18, 1994.

Jouvenne et al., "High levels of neutralizing autoantibodies against IL-1 alpha are associated with a better prognosis in chronic polyarthritis: a follow-up study," Scand. J. Immunol. 46, 413-18, Oct. 1997.

Lindqvist et al., "Prognostic laboratory markers of joint damage in rheumatoid arthritis," Ann. Rhem. Dis. 64, 196-201, Feb. 2005; Epub Sep. 30, 2004.

Ogush et al., "Autoantibodies to IL-1alpha in sera from rapidly progressive idiopathic pulmonary fibrosis," J. Med. Investigation 48, 181-89, Aug. 2001.

Ross et al., "High Avidity IFN-neutralizing Antibodies in Pharmaceutically Prepared Human IgG," J. Clin. Invest. 95, 1974-78, May 1995.

Ross et al., "Increased in Vivo Antibody Activity Against Interferon α, Interleukin-1α, and Interleukin-6 After High-Dose Ig Therapy," Blood 90, 2376-80, Sep. 15, 1997.

Satoh et al., "Characterization of anti-IL-1α autoantibodies in the sera from healthy humans," Immunopharmacol. 27, 107-18, 1994.

Saurat et al., Anti-interleukin-1α autoantibodies in humans: Characterization, isotype distribution, and receptor-binding inhibition—Higher frequency in Schnitzler's syndrome (urticaria and macroglobulinemia), J Allergy Clin Immunol. Aug. 1991;88(2):244-56.

Suzuki et al., "Demonstration of neutralizing autoantibodies against IL 1 alpha in sera from pateitns with rheumatoid arthritis," J. Immunol. 145, 2140-46, Oct. 1, 1990.

Svenson et al., "IgG Autoantibodies against Interleukin 1α in Sera of Normal Individuals," Scand. J. Immunol. 29, 489-92, 1989.

Svenson et al., "Distribution and Characterization of autoantibodies to Interleukin 1α in Normal Human Sera," Scand. J. Immunol. 32, 695-701, 1990.

Svenson et al., "Binding of Cytokines to Pharmaceutically Prepared Human Immunoglobulin," J. Clin. Invest. 92, 2533-39, Nov. 1993.

Svenson et al., "Effects of human anti-IL-1α autoantibodies on receptor binding and biological activities of IL-1," Cytokine 4, 125-33, Mar. 1992.

Svenson et al., "Antibody to Granulocyte-Macrophage Colony-Stimulating Factor Is a Dominant Anti-Cytokine Activity in Human IgG Preparations," Blood 91, 2054-61, Mar. 15, 1998.

Svenson et al., "Cytokine vaccination: neutralizing IL-1α autoantibodies induced by immunization with homologous IL-1α," J. Immunol. Methods 236, 1-8, 2000.

Waehre et al., "Increased Expression of Interleukin-1 Coronary Artery Disease with Downregulatory Effects of HMG-CoA Reductase Inhibitors," Circulation 109, 1966-7, 2004 (published online Mar. 29, 2004).

Merhi-Soussi et al: "Interleukin-1 plays a major role in vascular inflammation and atherosclerosis in male apolipoprotein E-knockout mice," Cardiovascular Res., 2005, pp. 583-593, vol. 66.

Ross et al: "Increased in vivo antibody activity against interferon alpha, interleukin-1alpha, and interleukin-6 after high-dose Ig therapy," Blood, 1997, pp. 2376-2380, vol. 90, No. 6.

Ito et al: "Interleukin 1alpha acts as an autocrine growth stimulator for human gastric carcinoma cells," Cancer Research, 1993, pp. 4102-4106, vol. 53.

Shirakawa et al: "Autocrine stimulation of interleukin 1alpha in the growth of adult human t-cell leukemia cells," Cancer Res., 1989, pp. 1143-1147, vol. 49.

Apte et al: Effects of micro-environment- and malignant cell-derived interleukin-1 in carcinogenesis, tumour invasiveness and tumour-host interactions, European Journal of Cancer, 2006, pp. 751-759, vol. 42.

Dinarello et al: "The role of interleukin-1 in disease," The New England Journal of Medicine, 1993, pp. 106-113, vol. 328, No. 2.

Mariotti et al: "Interleukin 1 alpha is a marker of endothelial cellular senescent," Immunity & Ageing, 2006, vol. 3, No. 4.

Niki et al: "Membrane-associated IL-1 contributes to chronic synovitis and cartilage destruction in human IL-1alpha transgenic mice," The Journal of Immunology, 2004, pp. 577-584.

McHale et al: "TNF-alpha and IL-1 sequentially induce endothelial ICAM-1 and VCAM-1 expression in MRL/lpr Lupus-Prone Mice," The Journal of Immunology, 1999, pp. 3993-4000, vol. 163.

Sandborg, et al: "Modulation of IL-1alpha, IL-1beta, and 25K Mr Non-IL-1 activity released by human mononuclear cells," Journal of Leukocyte Biology, 1989, pp. 417-427, vol. 46.

GenBank entry AY510107.1, 2005 (retrieved from the Internet on Apr. 23, 2010, <http://www.ncbi.nlm.nih.gov/nuccore.

Sunahara et al: "Differential determination of recombinant human interleukin-1 alpha and its deamidated derivative by two sandwich enzyme immunoassays using monoclonal antibodies. Comparison with a polyclonal antibody-based competitive enzyme immunoassay," Journal Immunol Methods, 1989, pp. 75-82; (Abstract only).

Simard, U.S. Appl. No. 13/162,705, filed Jun. 17, 2011 (not yet published).

Simard, U.S. Appl. No. 13/215,464, filed Aug. 23, 2011 (not yet published).

Simard, international patent application No. PCT/US11/40819, filed on Jun. 17, 2011 (not yet published).

Simard, international patent application No. PCT/US11/48747, filed on Aug. 23, 2011 (not yet published).

Horai, R. et al., Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J. Exp. Med, 1998, vol. 187, No. 9:1463-1475.

Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.

Braddock, M. et al., Therapeutic potential of targeting IL-1 and IL-18 in inflammation, Expert Opin. Biol. Ther., 2004, vol. 4, No. 6:8476-860.

Eugui, E. et al.: "Antibodies against membrane interleukin 1alpha activate accessory cells to stimulated proliferation of T lymphocytes," Proc, Natl. Acad. Sci, 1990, vol. 87:1305-1309.

Janeway, C.A. et al.: "The induction and detection of immune responses," ImmunoBiology The Immune System in Health and Disease, 3rd Edition, 1997.

* cited by examiner

DIAGNOSIS, TREATMENT, AND PREVENTION OF VASCULAR DISORDERS USING IL-1 AUTOANTIBODIES

This application is a National Stage application of co-pending PCT application PCT/IB2006/002038 filed on Jul. 26, 2007, which was published in English under PCT Article 21(2) as WO2007015128 on Feb. 9, 2007, and which claims the benefit of Ser. No. 60/704,450 filed on Aug. 2, 2005. These applications are incorporated herein by reference in their entireties.

FIELD OF THE INVENTION

The invention relates to diagnosis, treatment, and prevention of vascular disorders. More specifically, the invention relates to use of IL-1α autoantibodies to diagnose, treat, and prevent vascular disorders.

BACKGROUND OF THE INVENTION

For decades atherosclerosis has been investigated for its role in at least three diseases, heart disease (HD), peripheral arterial disease (PAD) and cerebrovascular disease (CD). The pathologic processes in these disease categories are similar, and atherosclerosis is now considered a systemic disease irrespective of which vascular bed is affected. Consequently, the social burden of atherosclerosis is enormous: in 2002 there were an estimated 71,100,000 persons in the US affected with heart disease, resulting in 947,428 deaths at a cost of US $393.5 billion dollars. There are 5,400,000 Americans living with the effects of stroke, costing an estimated $56.8 in healthcare in 2005. The global burden of atherosclerosis is expected to rise.

Atherosclerosis is a systemic disease. In many patients it is both insidious and affects more than one vascular bed. Early detection of atherosclerosis or identification of patients susceptible to developing atherosclerosis is crucial to preventing morbidity and mortality. There is, therefore, a need in the art to identify methods of identifying patients at risk for developing atherosclerosis as well as methods of treating patients already affected with an atherosclerosis-related disorder.

DETAILED DESCRIPTION OF THE INVENTION

The present invention relates to the observation that a high titer of IL-1α autoantibodies in humans reduces the risk of ischemic heart disease or its progression to coronary heart disease. The present invention provides a powerful means of detecting an individual at risk for developing atherosclerosis or an atherosclerosis-related disorder by determining the individual's IL-1α autoantibody titer. The invention also provides methods of using IL-1α autoantibodies to reduce risk, progression, or symptoms of vascular disease (e.g., coronary heart disease, peripheral arterial disease, and cerebrovascular disease).

IL-1α is released in sufficient quantities to induce high-affinity, high titer, neutralizing antibody responses in as many as 50% of patients analyzed, primarily in older men. Hansen et al., Eur. J. Clin. Invest. 24, 212-18, 1994. Furthermore, the ability of individuals to develop IL-1α autoantibodies provides a protective effect against some unknown role of IL-1α in the progression of pathological inflammatory processes in the arterial wall (atherosclerosis).

The correlation between risk of vascular disorders and IL-1α autoantibody titers is surprising because IL-lot is believed to exert its biological actions primarily at an intracellular level, as an autocrine substance, in the close vicinity of the cell producing IL-1α as a membrane-associated molecule, or as a strictly paracrine substance. Moreover, there is no current mechanism to explain the role of IL-1α in the progression of atherosclerosis. Thus, it is unexpected that an antibody targeting IL-1α would be of therapeutic value in the treatment or prevention of vascular diseases.

IL-1α Autoantibodies

"IL-1α autoantibodies" according to the invention include full-length antibodies isolated from B cells (including activated and/or immortalized B cells), blood, serum, or plasma; functional antibody fragments containing IL-1α binding sites of full-length IL-1α autoantibodies (e.g., F(ab)'$_2$ fragments, F(ab)' fragments, Fab fragments, double-stranded Fv fragments, and single-chain antibodies); recombinant immunoglobulin molecules produced by expressing cDNA derived from B cells or by expressing synthetic nucleotide sequences which encode the immunoglobulin molecules; monoclonal autoantibodies (produced as described below); and synthetic IL-1α autoantibodies (produced as described below). An IL-1α autoantibody typically is an IgG molecule, particularly an IgG$_4$ molecule (Garrone et al., Mol. Immunol. 33, 649-58, 1996), but can be an IgM, IgE, IgA, or IgD molecule. IL-1α autoantibodies also include any of the molecules described above which are coupled to another molecule (such as a receptor, ligand, enzyme, toxin, carrier, etc.) and autoantibodies made by combining the variable portions of an autoantibody of one isotype with the constant regions of another isotype.

IL-1α autoantibodies preferably bind with high affinity to IL-1α. High affinity IL-1α autoantibodies typically have an equilibrium affinity constant ($K_a$, or the reciprocal of $K_D$) for IL-1α binding of between $10^{14}$ M$^{-1}$ and $5 \times 10^{-7}$ M$^{-1}$ (e.g., $5 \times 10^7$, $10^{-13}$, $5 \times 10^{-8}$, $10^{-12}$, $5 \times 10^8$, $10^9$, $5 \times 10^9$, $10^{10}$, $5 \times 10^{10}$, $10^{11}$, $5 \times 10^{11}$, $10^{12}$, $5 \times 10^{12}$, $10^{13}$, or $5 \times 10^{13}$ M$^{-1}$). Specific binding of an IL-1α autoantibody to IL-1α can be determined using any appropriate method including, for example, technologies such as real-time Bimolecular Interaction Analysis (BIA) (Sjolander & Urbaniczky, Anal. Chem. 63, 2338-45, 1991, and Szabo et al., Curr. Opin. Struct. Biol. 5, 699-705, 1995). $K_a$ can be calculated from a Scatchard plot of specific binding data, as is known in the art. See also U.S. Pat. No. 5,959,085.

IL-1α autoantibodies of the invention preferably neutralize IL-1α bioactivity (e.g., IL-1α-induced IL-2 secretion) in vitro and in vivo. More preferably, IL-1α autoantibodies reduce or eliminate binding of IL-1α to its receptor. Neutralizing activity and receptor binding activity can be assayed as described in Satoh et al., Immunopharmacology 27, 107-18, 1994.

The methods and compositions described below encompass human IL-1α autoantibodies as well as IL-1α autoantibodies of other mammals including, but not limited to, other primates (e.g., gorillas, chimpanzees, baboons, squirrel monkeys), companion animals (e.g., cats, rabbits, dogs, horses), farm animals (e.g., cows, sheep, swine, goats, horses), and research animals (e.g., cats, dogs, guinea pigs, rabbits, sheep, goats, swine, chimpanzees, and baboons).

Methods of Obtaining IL-1α Autoantibodies

IL-1α autoantibodies can be obtained by a variety of methods. In some embodiments, preparations of polyclonal IL-1α autoantibodies are obtained from B cells, blood, plasma, or serum, either from a single individual or from pooled samples from 2 or more individuals. Sources of B cells include peripheral blood, tonsils, adenoids, and spleen. See U.S. Pat. No. 5,959,085. The individual(s) can be healthy or can have an autoimmune disease, particularly an autoimmune disease in which IL-1α autoantibodies are overproduced. These diseases include, e.g., Schnitzler's syndrome (Saurat et al., *J. Allergy Clin. Immunol.* 88, 244-56, 1991), autoimmune blistering disorders (e.g., pemphigus/phemphigoid) (Garrone et al., 1996), and chronic inflammatory arthritis (Garrone et al., 1996). Blood donors which are positive for the presence of circulating IL-1α autoantibodies can be identified using known methods, such as ELISA, radioimmunoprecipitation, Western blot, etc. See, e.g., Satoh et al., 1994; Saurat et al., 1991; Svenson et al., *J. Clin. Invest.* 92, 2533-39, 1993; Bendtzen et al., *Mol. Biotechnol.* 14, 251-61, 2000; Svenson et al., *Scand. J. Immunol.* 29, 489-92, 1989; Svenson et al., *Scand J. Immunol.* 32, 695-701, 1990; Svenson et al., *J. Clin. Invest.* 92, 2533-39, 1993; and Svenson et al., *Cytokine* 4, 125-33, 1992. In some embodiments, plasma is obtained using plasmapheresis or apheresis.

In some embodiments, donor serum is screened using an IL-1α enzyme-linked immunoadsorbant assay (ELISA). Because very low free IL-1α in the serum will correlate with the presence of neutralizing autoantibodies against IL-1α, the test allows for very quick screening and short-listing of donor serum for those with the high potential for providing appropriate neutralizing antibodies. This approach can simplify the initial screening process and reduce development time. IL-1α assay kits are available, for example, from Abazyme LLC; Alpco Diagnostics; Antigenix America Inc.; Autogen Bioclear UK Ltd; Bender MedSystems; Biosource International; BioVision; Cayman Chemical; Cell Sciences; CHEMICON; CytoLab Ltd., Endogen; GE Healthcare (formerly Amersham Biosciences); Leinco Technologies, Inc.; PeproTech; and R&D Systems.

IL-1α autoantibodies can be purified from individual or pooled blood, plasma, or serum using methods well known in the art, such as ultrafiltration, dialysis, washing after immobilization on a non-specific protein support, or affinity chromatography on a specific protein support. See US 2005/0147603. Human IL-1α autoantibodies can be purified from commercial preparations of human IgG (e.g., SANDOGLOBULIN® (Sandoz, Copenhagen, Denmark), GAMMGARD® (Baxter, Allerød, Denmark), or NORDIMMUN® (Novo Nordisk, Bagsvaerd, Denmark). See Ross et al., *J Interferon Res.* 14, 159-60, 1994; Svenson et al., *J. Clin. Invest.* 92, 2533-39, 1993. Affinity purification of IL-1α autoantibodies is described, for example, in Satoh et al., 1994.

In some embodiments, pools of plasma or serum collected from, e.g., 100 donors can be tested for binding of radiolabeled IL-1α to IgG using Protein G affinity chromatography. A suitable radiolabel is $^{125}$I. The radiolabeled tracer is observed for binding to IgG in pools, and recovery of added natural IL-1α to these pools can be assessed using an IL-1α ELISA. Plasma or serum of donors contributing to a positive pool can be reassessed individually and saturable binding of IL-1α to IgG in 10% of the plasma (judged by saturation binding of radiolabeled IL-1α to IgG) can be determined. For example, dilutions of donor plasma highly positive for IL-1α autoantibodies can be incubated with $^{125}$I-labeled IL-1α (3,500 cpm) in a final volume of 200 µl. IgG-bound tracer can be assessed by Protein G affinity chromatography. IgG-bound and free $^{125}$I-labeled IL-1α can be separated by secondary antibody precipitation. Average dissociation or affinity constants and maximal IL-1α IgG-binding capacities can be calculated using Scatchard plots.

Donors with highly positive sera, i.e., those harboring IL-1α autoantibodies with picomolar avidity at plasma antibody concentrations between 0.1 nM and 35 nM, can be used to harvest IL-1α autoantibody-producing B lymphocytes from peripheral blood. However, useful IL-1α autoantibodies may exhibit a range of avidity, from femptomolar to nanomolar avidity, which may be considered useful for therapeutics, depending on the target and desired pharmacokinetics of the antibody therapeutic. Plasma concentrations of IL-1α autoantibodies may range significantly and, depending on the sensitivity and efficiency of cloning or enrichment, may be in the range of 0.1 picomolar to 0.1 nanomolar, or conversely may be in high concentrations in the range 35 nM to 3500 nm, as is the case for plasma B cell malignancies. Peripheral blood lymphocytes which produce IL-1α autoantibodies can be stimulated to grow in culture and, therefore, can be immortalized using methodologies well known in the art using, for example, a virus (e.g., Epstein Barr virus, EBV), a chemical agent, or a nucleic acid (such as an oncogene). The immortalized cells can then be cloned using known methods to provide a reliable source of large amounts of human IL-1α autoantibodies.

In some embodiments, B lymphocytes from blood samples of appropriate donors are immortalized in bull culture with EBV in the presence of irradiated mononuclear cells and a toll-like receptor agonist (such as a CpG oligonucleotide), which acts as a polyclonal activator of memory B cells and increases their susceptibility to EBV infection. Immortalized B lymphocytes are then selected for IgG-positive memory B lymphocytes by a combination of magnetic and fluorescence-activated cell sorting. Supernatants from cultures containing 10 IgG-positive memory B cells can be analyzed after 12-14 days for the presence of specific IL-1α autoantibodies. Positive cultures are re-plated, and limiting dilution is used to isolate individual immortalized B lymphocyte clones with appropriate production of IL-1α autoantibodies. See, for example, WO 91/09115 and U.S. Pat. No. 5,959,085.

In other embodiments, isolated lymphocytes are used to produce hybridomas as is well known in the art. (See, e.g., Methods in Enzymology, Vol. 121, Sections I and II, 1986; Garrone et al., 1996). Hybridomas which produce IL-1α autoantibodies can be propagated in vitro as is known in the art to provide a constant source of the autoantibodies. Alternatively, hybridoma cells can be injected intraperitoneally into mice, which will then produce tumors. These tumors are accompanied by the production of ascites fluid which contains the desired monoclonal autoantibodies. The monoclonal autoantibodies can be recovered from the ascites fluid by conventional methods such as ultrafiltration, ultracentrifugation, dialysis, and immunoaffinity chromatography.

RNA can be obtained from an immortalized B cell clone or a hybridoma clone and used as a template for an amplification reaction (e.g., PCR) to obtain cDNA encoding for an IL-1α autoantibody. See U.S. Pat. No. 5,959,085. cDNA encoding a full-length IL-a autoantibody or a functional fragment thereof can be included in an expression vector and used to express the IL-1α autoantibody in prokaryotic or eukaryotic host cells using recombinant DNA methodologies well known in the art. See, e.g., Garrone et al., 1996. The host cells can then be used to propagate the IL-1α autoantibody. Alternatively, any particular IL-1α autoantibody can be isolated and its amino acid sequence determined by known methods. Nucleic acid molecules which encode the amino acid sequence can be synthesized and used in an expression vector to produce cloned IL-1α autoantibodies. If desired, the original heavy chain constant region of an IL-1α autoantibody can be replaced by a constant region of a different isotype (e.g., $IgG_1$, $IgG_2$, $IgG_3$, $IgG_4$, IgA, IgD, IgM, or IgE). See U.S. Pat. No. 5,959,085.

IL-1α autoantibodies can be chemically synthesized using techniques known in the art. See, e.g., Merrifield, *J. Am. Chem. Soc.* 85, 2149-54, 1963; Roberge et al., *Science* 269, 202-04, 1995. Protein synthesis can be performed using manual techniques or by automation. Automated synthesis can be achieved, for example, using Applied Biosystems 431A Peptide Synthesizer (Perkin Elmer). Optionally, fragments of an IL-1α autoantibody can be separately synthesized and combined using chemical methods to produce a full-length molecule.

IL-1α autoantibodies can be obtained by screening antibody libraries, such as HuCAL® (Knappik et al., *J. Mol. Biol.* 296, 57-86, 2000), scFv phage display libraries (e.g., Pharmacia Recombinant Phage Antibody System, catalog no. 27-9400-01; and the Stratagene SURZAP™ phage display kit, catalog no. 240612), and the like. See WO 92/18619; WO 92/20791; WO 93/01288; WO 92/01047; WO 92/09690; Fuchs et al., *Bio/Technology* 9, 1370-72, 1991; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:357&3580; Garrad et al. (1991) Bio/Technology 9:1373-1377; Hoogenboom et al. (1991) Nuc Acid Res 19:4133-4137; and Barbas et al. (1991) PNAS 88:7978-7982.

If desired, modifications can be made to IL-1α autoantibodies to enhance their binding affinity for IL-1α. See, e.g., U.S. Pat. No. 6,914,128.

Screening Methods

According to the invention, a low titer of IL-1α autoantibodies or the presence of low affinity human anti-IL-1α autoantibodies indicates a likelihood that the individual will progress to an atherosclerosis-related disorder or that the severity of the individual's atherosclerosis-related disorder will increase. An individual has a "low titer" of IL-1α autoantibodies if a positive response in an immunoassay (e.g., a radioimmunoassay, ELISA, or Western blot) is detected at a dilution of the individual's serum of no more than about 1:100 (e.g., a dilution of 1:1, 1:10, 1:50, or 1:100). An individual has a "high titer" of IL-1α autoantibodies if a positive response in an immunoassay can still be detected at a dilution of more than about 1:100 (e.g., 1:1000, 1:10,000, 1:100,000, etc.). Low affinity IL-1α autoantibodies typically have a K for IL-1α binding of between 10 $M^{-1}$ and $10^7 M^{-1}$ (e.g., 10, $5 \times 10^2$, $10^3$, $5 \times 10^3$, $10^4$, $5 \times 10^4$, $10^5$, $5 \times 10^5$, $10^6$, $5 \times 10^6$, and $10^7 M^{-1}$).

A test biological sample (comprising, e.g., blood, plasma, serum) from an individual can be assayed to determine a test titer of IL-1α autoantibodies. The individual can be healthy, or apparently healthy, or can be known to have an atherosclerosis-related disorder. The atherosclerosis-related disorder can be, for example, cerebral vascular disease, peripheral vascular disease, ischemic heart disease, or coronary artery disease.

Any method known in the art can be used to detect IL-1α autoantibodies in the individual's test biological sample. These methods include, but are not limited to, binding to radiolabeled IL-1α, ELISA, competitive binding of IL-1α to its receptor, FITC-labeled IL-1α using flow cytometry, Western blot, etc. See, e.g., Bendtzen et al., *Mol. Biotechnol.* 14, 251-61, 2000; Ross et al., *Blood* 90, 2376-80, 1997; Hansen et al., *Immunol. Lett.* 30, 133, 1991; Svenson et al., *Scand. J. Immunol.* 29, 489-92, 1989; Svenson et al., *Scand J. Immunol.* 32, 695-701, 1990; Svenson et al., *Cytokine* 4, 125-33, 1992; Saurat et al., *J. Allergy Clin Immunol.* 88, 244-56, 1991. Radioimmunoassays, such as those described in Bendtzen et al., *Mol. Biotechnol.* 14, 251-61, 2000, are preferred. Titers of autoantibodies to IL-1α in a test biological sample can be calculated using standard methods known in the art. Assays can be carried out either qualitatively or quantitatively. Alternatively, using FITC-labeled IL-1α for identification of B lymphocytes expressing an IL-1α autoantibody, IL-1α-specific B lymphocyte frequency can be correlated with serum IL-1α levels and thus be an indicator of the risk of developing atherosclerosis or a related disorder.

Pharmaceutical Compositions and Therapeutic Methods

Pharmaceutical compositions of the invention comprise high affinity IL-1α autoantibodies as defined above. The IL-1α autoantibodies can be derived from a single source (for example, a single individual, a clone of an immortalized B cell clone, or a single hybridoma) or from two or more such sources, including two or more preparations of monoclonal IL-1α autoantibodies or a mixture of monoclonal and polyclonal IL-1α autoantibodies. Pharmaceutical compositions are non-pyrogenic.

Pharmaceutically Acceptable Vehicles

"Pharmaceutically acceptable vehicles" include any and all solvents, dispersion media, coatings, antibacterial and antifungal agents, isotonic and absorption delaying agents, and the like which are physiologically compatible. Examples of pharmaceutically acceptable vehicles include one or more of water, saline, phosphate buffered saline, dextrose, glycerol, ethanol, etc., as well as combinations thereof. In cases one or more isotonic agents are included, such as sugars, polyalcohols such as mannitol, sorbitol, or sodium chloride. Pharmaceutically acceptable vehicles may further comprise minor amounts of auxiliary substances such as wetting or emulsifying agents, preservatives, or buffers, which enhance the shelf life or effectiveness of the IL-1α autoantibodies.

Pharmaceutical compositions of this invention may be in a variety of forms. These include, for example, liquid, semisolid and solid dosage forms, such as liquid solutions (e.g., injectable and infusible solutions), dispersions or suspensions, tablets, pills, powders, liposomes and suppositories. The preferred form depends on the intended mode of administration and therapeutic application.

For example, IL-1α autoantibodies can be lyophilized into a highly pure crystalline form. The final product can be supplied as a sterile, lyophilized powder suitable for reconstitution and parenteral infusion. Lyophilized powder can be contained in sterile vials, each containing between, e.g., 1-1000 mg of IL-1α autoantibodies. Each vial can contain additional non-medical ingredients, such as one or more of the following; sucrose, polysorbate 80, monobasic sodium phosphate, monohydrate, polyethylene glycol and dibasic sodium phosphate and dihydrate.

In some embodiments, IL-1α autoantibodies in a vial can be reconstituted immediately prior to use with, for example, 1-30 mL of Sterile Water for Injection, USP, with a resulting pH of approximately 7.2. Preservatives can be included. If the product does not contain preservatives, the product typically is used immediately after reconstitution and not re-entered or stored. The total dose of the reconstituted product can be further diluted to 50-500 mL with 0.9% Sodium Chloride Injection, USP. The infusion concentration can range between 0.04 mg/mL and 40 mg/mL. Infusion can begin, for example, within about 1-4 hours after reconstitution. Preferably, the infusion solution is administered over a period of about 2 hours using an infusion set with an in-line, sterile, non-pyrogenic, low-protein-binding filter (pore size of 1.2 μm or less).

In other embodiments, Il-1α autoantibodies are formulated into a pharmaceutical composition suitable for parenteral administration, for example, as an injectable solution. IL-1α autoantibodies can be in a liquid or lyophilized dosage form, for example, in a flint or amber vial, ampule, or pre-filled syringe. Suitable buffers include L-histidine, sodium succinate, sodium citrate, sodium phosphate, and potassium phosphate. Sodium chloride can be used to modify the toxicity of the solution at a concentration of 0-300 mM (e.g., 150 mM for a liquid dosage form). Cryoprotectants can be included for a lyophilized dosage form (e.g., 0-10% sucrose, trehalose, or lactose). Bulking agents, such as mannitol, also can be included for a lyophilized dosage form. Stabilizers such as L-methionine can be used in both liquid and lyophilized dosage forms. Surfactants, e.g., polysorbate 20 and BRIJ surfactants, can be included.

Pharmaceutical compositions of the invention can be used to treat atherosclerosis-related disorders, including ischemic heart disease, coronary artery disease, peripheral arterial disease, and cerebrovascular disease. Individuals preferably are treated with pharmaceutical preparations comprising autoantibodies of the same species (i.e., humans are treated with human IL-1α autoantibodies). A therapeutically effective amount of a pharmaceutical composition according to the invention can be administered to an individual having symptoms of one or more of these disorders or can be administered prophylactically to individuals at risk for developing one or more of these disorders. A "therapeutically effective amount" is an amount which reduces the amount of free IL-1α in the individual's serum or which raises an individual's IL-1α autoantibody titer by at least two-fold. Preferably, the individual's symptoms of an atherosclerosis-related disorder are reduced (e.g., cramping in hips, thighs or calves; angina).

Pharmaceutical compositions of the invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In some embodiments, the Il-1α autoantibodies can be prepared with a carrier that will protect the autoantibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Both the dose and the administration schedule of pharmaceutical preparations of the invention will vary depending on the individual's risk of developing an atherosclerosis-related disorder, the symptoms and severity of an individual's disease, and the individual's species. Typical doses of IL-1α autoantibodies are in the range of 0.001 µg to 400 mg/kg (e.g., 0.001 µg, 0.01 µg, 0.1 µg, 0.5 µg, 1.0 µg, 10 µg, 100 µg, 1 mg, 2 mg, 5 mg, 10 mg, 15 mg, 20 mg, 25 mg, 50 mg, 75 mg, 100 mg, 150 mg, 200 mg, 250 mg, 300 mg, 350 mg, or 400 mg). The dose can be administered, for example, daily for 4 days, once weekly, twice monthly, monthly, once every 12 weeks, once every 24 weeks, or once every 90 days.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Correlation of Ischemic Heart Disease with Il-1α Autoantibody Titer

Serum samples from men enrolled in the Copenhagen Male Study (CMS; Gyntelberg, Dan Med Bull 1973; 20:1-4) were examined for IL-1α autoantibody titer. The men ranged in age from 53 to 75 years (mean=63). The results are shown in Table 1.

TABLE 1

| quintile (no. individuals) | aAb-IL-1α titer | percent with ischemic heart disease at 10 year follow-up |
| --- | --- | --- |
| 1 (132) | 0 | 20.5% |
| 2-4 (379) | low | 18.7% |
| 5 (137) | high | 12.2% |

As indicated in Table 1, at the 10-year follow-up of these patients there was a decreased incidence of ischemic heart disease in those individuals having high IL-1α autoantibody titers.

EXAMPLE 2

Autoantibodies to Il-1α in Patients with Ischemic Heart Disease

Sera from 20 patients were studied within 3 days of coronary artery bypass surgery and compared with 20 age-matched males without signs of ischemic heart disease. The results are shown in Table 2.

TABLE 2

|  | males with ischemic heart disease | healthy males | total |
| --- | --- | --- | --- |
| +IL-1α autoantibodies | 0 | 12 | 12 |
| −IL-1α autoantibodies | 20 | 8 | 28 |
|  | 20 | 20 | 40 |

$P < 0.0001$ (Fisher's exact test, two-sided)

EXAMPLE 3

Isolation and Stimulation of Mononuclear Cells

This example describes one suitable method for isolating and stimulating mononuclear cells. Mononuclear cells (MNC) from healthy blood donors is obtained using donors negative for IL-1α autoantibodies. MNC are purified from buffy coats by centrifugation on LYMPHOPREP™ (Nycomed). Cells are washed in RPMI 1640 containing 2 mM L-glutamine (Sigma, St. Louis, USA), 25 µg/ml gentamycin (GIBCO® BRL, Life Technologies, Paisley, Scotland) and 5% normal human AB serum. Native IL-1α (nIL-1α) is generated by stimulating MNC at 37° C. in 5% $CO_2$ humidified air in the presence of 100 µg/ml E. coli LPS (Difco Laboratories, Detroit, USA). After 12 h, the supernatant is harvested and stored at −20° C. until use.

Protein G Affinity Chromatography

Affinity chromatography of 100 µl plasma samples is carried out at 4° C. using columns containing 2000 µl Protein G Sepharose 4 Fast Flow (Amersham Biosciences). Phosphate-buffered saline pH 7.4 (PBS) supplemented with 0.1% (v/v) Triton X-100 and 0.1% (w/v) gelatin (Sigma) is used as running buffer. Bound material is eluted with 0.1 M glycine/HCl, pH 2.4.

Specificity Analyses

Antibody specificity analyses are carried out with different preparations of natural and recombinant IL-1α together with radiolabeled rIL-1α. Plasma samples which are positive for anti-IL-1α are diluted to bind approximately 60% of a total of 15 ng/200 µl IL-1α, including both unlabeled IL-1α and tracer IL-1α (15 pg/200 µl $^{125}$I-labeled IL-1α). The mixture of plasma, tracer, and competitor is pre-incubated for 1 h at 37° C. and then subjected to affinity chromatography on Protein G. Fractions corresponding to IgG-bound and free tracer are counted in a gamma counter (1470 WIZARD™ gamma counter, Wallac, Finland). In addition, free IL-1α is measured by ELISA.

Screening Plasma Samples by RIA and ELISA

Plasma samples are collected from individual blood donors according to appropriate protocols and quality control of blood components. Samples are initially mini-pool screened for anti-IL-1α. Mini-pools of 90 plasma samples are adjusted to 25% (v/v) in PBS supplemented with 0.1% (v/v) Triton X-100 (Sigma), 0.1% (w/v) gelatin (Sigma) and 2 mM EDTA (Bie & Berntsen, Rødovre, Denmark) (PBS+), and 3,500 cpm $^{125}$I-labeled IL-1α is added; there is a final volume of 200 µl. After incubation for 20 h at 4° C., fractions representing IgG-bound tracer and free tracer are separated by Protein G and counted. In addition, anti-IL-1α binding activity is addressed with regard to natural IL-1 α. This can be done by measuring recovery of 1 ng/ml natural IL-1α in the presence of 25% plasma pools in an IL-1α ELISA.

IL-1α ELISA

This sandwich ELISA is based on specific polyclonal rabbit anti-human IL-1α antibodies. It has been validated thoroughly with respect to interference from natural human IL-1α antibodies. See Hansen et al., Scand. J. Immunol. 1991. 33: 777-781; Hansen et al., Cytokine 1993.5: 72-80:

IMMUNO® MAXISORP® plates (Nunc, Roskilde, Denmark) are coated with Protein A affinity-purified rabbit anti-human IL-1α IgG. Non-attached sites are blocked with PBS containing 4% (w/v) skimmed milk powder, 1% (w/v) human serum albumin (HSA) (SSI, Copenhagen, Denmark) and 0.005% (v/v) TWEEN® 20 (Merck). The wells are washed with PBS/0.005% TWEEN® 20 after each of the following steps: 1) 100 µl analyte incubated for 18 h at 4° C.; 2) 100 µl biotinylated rabbit anti-human IL-1A IgG (2 µg/ml) in PBS/0.005% (v/v), TWEEN® 20/0.5% (w/v) HSA, incubated for 2 h at 20° C.; 3) 100 µl streptavidin-peroxidase (0.1 µg/ml; Kirkegaard & Perry Laboratories, Gaithersburg, USA) in PBS/0.005% (v/v) Tween 20/0.5% (w/v) HSA, incubated for 45 min at 20° C. Enzyme activities are quantitated using 1,2-phenylenediamine dihydrochloride (DakoCytomation). The working range of the ELISA is from 150 pg/ml to 5,000 pg/ml. The inter- and intra-assay coefficients of variation are maintained below 15%.

HS IL-1α ELISA

Plasma IL-1α levels are quantified using the IL-1A Quantikine High Sensitivity ELISA (R&D Systems, Minneapolis, Minn.). According to the manufacturer's validation and instructions, this ELISA detects IL-1α bound to both sIL-1αR and IL-1α autoantibodies.

Secondary Antibody Precipitation and Scatchard Plots

The binding characteristics of IL1α autoantibodies in selected antibody-positive plasma samples are assessed as previously described (Hansen et al., Eur. J. Immunol. 1995. 25: 348-354). Appropriately diluted plasma samples are mixed with $^{125}$I-labeled IL-1α ranging from 50,000 cpm to 700 cpm in PBS+ in a final volume of 100 µl. After incubation at 4° C. for 20 h, 200 µl rabbit anti-human IgG (A424; Dako-Cytomation) is added to precipitate more than 95% of the IgG. After incubation for 1 h at 4° C., three volumes of PBS is added. The samples are centrifuged immediately for 20 min (3000×g at 4° C.) after which the amounts of IL-1α in the pellets (IgG-bound) and the supernatants (free) are counted. Affinities of IL-1α autoantibodies for IL-1α binding are calculated using Scatchard plots.

The invention claimed is:

1. A method of screening a male individual to determine the individual's relative risk of developing ischemic heart disease, comprising:
    determining a test titer of IL-1α autoantibodies in a biological sample of the individual; and
    identifying the individual as having an increased risk of developing ischemic heart disease-if the test titer is lower than 1:100; or
    identifying the individual as having a decreased risk of developing ischemic heart disease if the test titer is higher than 1:100.

2. The method of claim 1 wherein the male individual is a human.

3. The method of claim 1 wherein the biological sample comprises blood or serum.

4. A method of raising the serum titer of IL-1α autoantibodies in an individual previously determined to have (i) atherosclerosis or a high risk of developing atherosclerosis and (ii) a low serum titer of IL-1α autoantibodies, the method comprising the step of: administering to the individual an amount of a pharmaceutical composition which consists essentially of: antibodies that target IL-1α and a pharmaceutically acceptable vehicle, wherein the amount of antibodies that target IL-1α is sufficient to raise the individual's serum titer of IL-1α autoantibodies at least two-fold.

5. The method of claim 4, wherein the IL-1α autoantibodies are monoclonal.

6. The method of claim 4, wherein the IL-1α autoantibodies have a $K_a$ for IL-1α of between $10^7$ and $10^{14} M^{-1}$.

7. The method of claim 4, wherein the individual is a human.

8. The method of claim 7, wherein the human is a male.

9. The method of claim 4, wherein the antibodies that target IL-1α are selected from the group consisting of F(ab)'$_2$ fragments, F(ab)' fragments, Fab fragments, double-stranded Fv fragments, and single-chain antibodies.

10. The method of claim 4, wherein the antibodies that target IL-1α are made by combining a variable portion of an autoantibody of one isotype with the constant region of another isotype.

11. The method of claim 4, wherein the antibodies that target IL-1α are obtained by screening a library.

12. The method of claim 4, wherein the antibodies that target IL-1α are recombinant immunoglobulin molecules produced by expressing cDNA derived from B cells or by expressing synthetic nucleotide sequences which encode the immunoglobulin molecules.

13. The method of claim 4, wherein the antibodies that target IL-1α are obtained from B cells, blood, plasma, or serum.

14. The method of claim 4, wherein the antibodies that target IL-1α are obtained from pooled samples from two or more individuals.

* * * * *